US012790296B2

(12) United States Patent
Durdagi et al.

(10) Patent No.: US 12,790,296 B2
(45) Date of Patent: Nov. 10, 2026

(54) DRG-MDM2-3 FOR USE AS A NOVEL MOUSE DOUBLE MINUTE 2 (MDM2) INHIBITOR

(71) Applicants: BAHCESEHIR UNIVERSITESI, Besiktas/Istanbul (TR); ISTANBUL TEKNIK UNIVERSITESI, Istanbul (TR)

(72) Inventors: Serdar Durdagi, Besiktas/Istanbul (TR); Muge Didem Orhan, Besiktas/Istanbul (TR); Timucin Avsar, Besiktas/Istanbul (TR); Maide Nur Paksoy, Besiktas/Istanbul (TR); Gulsah Aydin, Besiktas/Istanbul (TR); Mine Yurtsever, Besiktas/Istanbul (TR)

(73) Assignees: BAHCESEHIR UNIVERSITESI, Besiktas/Istanbul (TR); ISTANBUL TEKNIK UNIVERSITESI, Istanbul (TR)

( * ) Notice: Subject to any disclaimer, the term of this patent is extended or adjusted under 35 U.S.C. 154(b) by 849 days.

(21) Appl. No.: 17/904,423

(22) PCT Filed: Feb. 17, 2021

(86) PCT No.: PCT/TR2021/050145
§ 371 (c)(1),
(2) Date: Aug. 17, 2022

(87) PCT Pub. No.: WO2021/167572
PCT Pub. Date: Aug. 26, 2021

(65) Prior Publication Data
US 2023/0067644 A1 Mar. 2, 2023

(51) Int. Cl.
*C07D 209/04* (2006.01)
*A61K 45/06* (2006.01)

(52) U.S. Cl.
CPC ............ *C07D 209/04* (2013.01); *A61K 45/06* (2013.01)

(58) Field of Classification Search
CPC .... C07D 209/04; C07D 209/20; A61K 45/06; A61P 35/00
See application file for complete search history.

(56) References Cited

U.S. PATENT DOCUMENTS 4,000,297 A * 12/1976 Rovati ................. C07D 209/20 548/496

FOREIGN PATENT DOCUMENTS

| | | | |
|---|---|---|---|
| CN | 107235969 | A | 10/2017 |
| WO | 2017172368 | A1 | 10/2017 |

OTHER PUBLICATIONS

CAS Registry No. 13078-91-6 (which entered STN database on Nov. 16, 1984). (Year: 1984).*
CAS Registry No. 61-54-1 (which entered STN database on Nov. 16, 1984). (Year: 1984).*
Ogasawara et al. Screening of Natural Compounds for Inhibitory Activity on Colon Cancer Cell Migration (Biol. Pharm. Bull. 24(6) 720-723). (Year: 2001).*
Abdel-Fattah et al. MDM2/p53 protein expression in the development of colorectal adenocarcinoma (Journal of Gastrointestinal Surgery, 4(1), 2000, 109-114). (Year: 2000).*
Klein et al. Platinum Drug Distribution in Cancer Cells and Tumors (Chem. Rev. 2009, 109, 4911-4920). (Year: 2009).*
CAS Registry No. 1028126-69-3 (which entered the STN database on Jun. 13, 2008). (Year: 2008).*
International Search Report in International Application No. PCT/TR2021/050156 dated May 31, 2021.
Zhou, A., Yan, L., Lai, F., Chen, X., Goto. M., Lee, K. H., & Xiao, Z. (2017). Design, synthesis and biological evaluation of novel indolin-2-ones as potent anticancer compounds. Bioorganic & medicinal chemistry letters, 27(15). 3326-3331.
Sun, H.B., Wang, X. Y., Li, G. B., Zhang. L. D., Liu. J., & Zhao, L. F. (2015). Design, synthesis and biological evaluation of novel C3-functionalized oxindoles as potential Pim-1 kinase inhibitors.
Aydin, G., Paksoy, M. N., Orhan, M. D., Avsar, T., Yurtsever, M., & Durdagi, S. (2020). Proposing novel MDM2 Inhibitors: Combined physics-driven high-throughput virtual screening and in vitro studies. Chemical Biology & Drug Design. 96(1). 684-700.

* cited by examiner

*Primary Examiner* — Kamal A Saeed
*Assistant Examiner* — Meghan C Heasley
(74) *Attorney, Agent, or Firm* — RAPHAEL BELLUM PLLC

(57) ABSTRACT

The invention relates to compound shown with formula (I) or a pharmaceutically acceptable derivative thereof for use as a novel inhibitor of MDM2 activity.

14 Claims, 2 Drawing Sheets

DRG-MDM2-3 FOR USE AS A NOVEL MOUSE DOUBLE MINUTE 2 (MDM2) INHIBITOR

TECHNICAL BACKGROUND

Figure 1:
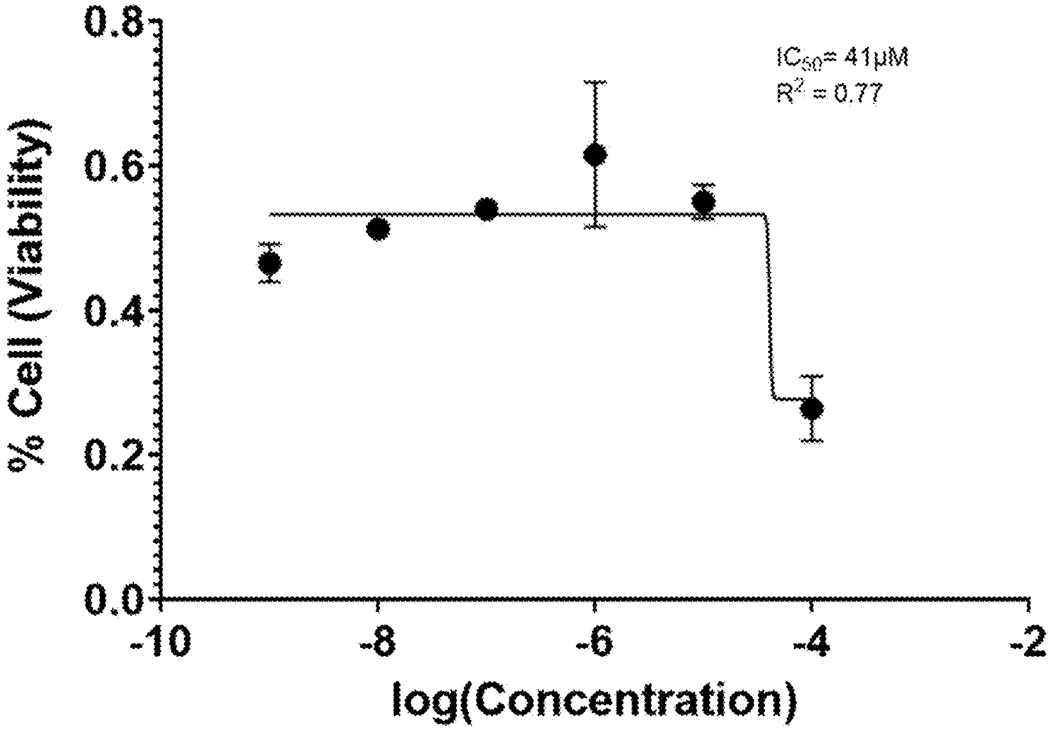

The p53 is an important gene that protects the cell cycle and acts as a tumor suppressor. It plays important roles in the regulation of cellular functions, DNA repair, neurodegenerative diseases, aging, ischemia, apoptosis and cell cycle arrest. Many of these p53 activities play a role in suppression of tumor by preventing oncogenic damage, repairing or eliminating oncogenic progressive cells. Loss of p53 function is associated with development of cancer in various organs. In the case of metabolic stress and increase of oncogenes, p53 levels are also increasing. Optimal increases in p53 levels are vital. However, excessive or insufficient p53 level is a clear sign of malfunctioning of the gene. Former causes apoptosis whereas latter leads to tumor formation. The natural negative regulator of p53 is the Mouse Double Minute 2 (MDM2), an endogenous p53 inhibitor. The MDM2 gene is a proto-oncogene that negatively regulates the transcriptional activation of p53 by p53 ubiquitination. This arrangement is very important to protect low levels of p53, maintaining normal cell cycle progression and cell survival. Thus, the most common p53 suppression mechanism involve the MDM2.

The p53 is an unstable protein with a half-life of 5-30 minutes in normal cells without stress. It is monoubiquitinated continuously by MDM2 to be broken down by proteasomes in the nucleus and cytoplasm. MDM2 is expressed in the nucleus under normal cellular conditions but can be displaced in the cytoplasm and mediated to disintegration by proteasomes of some targets such as p53. In case of cellular stress, the p53 pathway is activated and leads to tumor cell inhibition by inhibiting the proliferation of cells with oncogenic potential. The p53 pathway is mainly inactivated due to overexpression of endogenous negative regulators (especially MDM2). More than 17% of tumors present MDM2 gene amplification leading to poor prognosis and treatment failure in chemotherapeutics.

The significance of p53-MDM2 interaction was demonstrated by in vivo experiments. MDM2 amplification was observed in human sarcomas. Various approaches have been used to antagonize the p53 inhibition effect of the MDM2. These methods involve development of MDM2 antagonists which inhibit p53-MDM2 interactions. Thus, direct inhibition of MDM2 may cause inhibitory and therapeutic activity because it can inhibit both p53-dependent and p53-independent functions of MDM2. MDM2 levels increase in ovarian cancers, while it is very low in benign ovarian tumors and normal ovaries. The overexpressed MDM2 is directly bound to the N-terminal domain of p53 and inhibits with one of the following mechanisms: (i) Stimulate the ubiquitin-dependent p53 degradation in the nuclear and cytoplasmic 26S proteasomes by acting as E3 ubiquitin ligase; (ii) reducing the transcriptional ability of p53 by promoting the transport of p53 from the nucleus to the cytoplasm; (iii) interacting strongly with p53, reducing its ability to bind to DNA, which makes p53 transcriptionally dysfunctional. The irregularity of the p53-MDM2 pathway, including p53 mutations and deletions and/or MDM2 amplification and overexpression, is the most frequently observed molecular change in various human cancers. p53-MDM2 balance disruption can lead to malignant transformation of normal cells and may also affect chemosensitivity of tumor cells. MDM2 overexpression leads to the suppression of apoptotic function of p53 and hence uncontrolled proliferation of cancer cells.

MDM2 protein consists of four functional independent domains including N-terminal domain to which p53 is linked (nuclear localization sequence (NLS), the nuclear export sequence (NES), the Box-1 domain) (aa 19-102); central acidic domain (aa 223-274); zinc finger domain (aa 305-322) and RING finger domain which is critical for E3 ubiquitin ligase activity (aa 438-478).

STATE OF THE ART

The inhibition of p53-MDM2 interactions with small molecules has been highly suggested and numerous MDM2 inhibitors have been discovered, in recent years. The structural features of the p53-MDM2 complex leads for designing of small molecules that mimic key residues to prevent p53-MDM2 interactions. Nutlin compounds that are capable of inducing apoptosis in cancer cells and disrupting p53-MDM2 interaction and restoring p53 functions are the most well-known MDM2 antagonists. Nutlins are well-known compounds for their antitumor profiles in wild-type p53 cells. Selective nutlins for inhibition of p53-MDM2 interaction are cis imidazoline class of small molecules. The Nutlin derivative MI-219 (contains oxindole ring) induces apoptosis in cancer cells in vitro and in vivo by inhibiting the p53-MDM2 interactions. MI-219 has been shown to selectively inhibit the growth of wild-type p53-containing lung cancer cells by cell cycle arrest in the G1 or G2 phase. The analogue of MI-219 and nutlin-3a, an oxindole derivative (MI-319), is a synthetic small molecule that binds the MDM2 protein with 500-fold high binding affinity from a natural p53 peptide. Studies have shown that MI-319, in combination with the chemotherapeutic drug cisplatin, suppresses cell cycle growth synergistically and induces apoptosis in pancreatic cancer cell lines. 7-nitro-5-deazaflavin and deazaflavin-5 are powerful MDM2 E3 ligase inhibitors that perform the autoubiquitination of MDM2. Because of the medical importance of the oxindole and indole compounds, derivatives of these compounds having cytotoxic activity against cancer cell lines have been reported. Spiro-tetrahydrothiopyran oxindole scaffold was formed as an inhibitor of p53-MDM2 and showed a good potent as MDM2 inhibitor and antitumor activity. The antitumor activity of spirocyclic oxindole skeleton against human lung cancer cell A549, human liver cancer cell BEL7402 and human colon cancer cell HCT-8 was investigated. Indole derivatives have been shown to be potent and have high therapeutic activity against different cancer types. Some of the currently used FDA approved chemotherapeutics contain indole ring whose antitumor activities are evaluated at the clinical stage.

Even though there are certain molecules that are interfering with the p53 and MDM2 interaction there is still need for novel drugs with better pharmacokinetic profiles that can serve as MDM2 inhibitors such that p53 can show beneficial effect against uncontrolled tumor growth.

The inventors have found that a new compound shown with formula I acts as an inhibitor of p53-MDM2 interaction.

The compound shown with formula I according to present invention is thus a representative of a novel compound that is suitable for use in several disorders where an interaction of p53-MDM2 pathway plays a role. Such diseases can for example be proliferative diseases such as cancer. Therefore, present invention not only relates to novel compounds shown with formula I but also to use of said compounds for treatment of proliferative diseases such as cancer.

DETAILED DESCRIPTION OF THE INVENTION

The invention relates to compound shown with formula I, which is DRG-MDM2-3, or a pharmaceutically acceptable derivative thereof.

Formula I

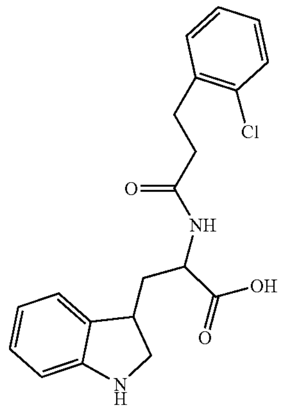

Unless specified otherwise, the terms "compound of the present invention" or "compound of invention" or "compound of formula I" or "compound shown with formula I" are used interchangeable and refer to compounds of formula I and salts thereof, hydrates or solvates of the compound of formula I or its salts, all stereoisomers (diastereomers and enantiomers), tautomers, isotopically labeled compounds (including deuterium substitutions), or its forms that form under physiological conditions of the human body, as well as inherently formed moieties (e.g., polymorphs, solvates and/or hydrates).

In other words, the term "pharmaceutically acceptable derivative thereof" refers to hydrates, solvates, prodrugs, all stereoisomers, salts, esters, tautomers, isotopically labeled derivatives or forms of compound of formula I that form under physiological conditions of the human body (for example, carboxylate anion form of compound of formula I, named as Formula Ia).

Formula Ia

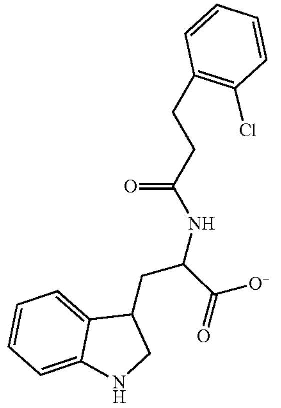

Several embodiments of the invention are described herein. It must be considered that each specified embodiment can be combined with other specified features to provide further embodiments. The terms used in the singular will also include plural and vice versa.

As disclosed herein the term "enantiomers" mean a pair of stereoisomers that are non-superimposable mirror images of each other. A 1:1 mixture of a pair of enantiomers is a "racemic" mixture. The absolute stereochemistry is specified according to the Cahn-Ingold-Prelog R—S system. When a compound is a pure enantiomer the stereochemistry at each chiral carbon may be specified by either R or S. Compound of formula I has a chiral center. In a preferred embodiment of the invention compound of formula I is in the form of a 1:1 racemic mixture of R and S enantiomers. The compound of formula I can also be in pure R form or in pure S form or a mixture thereof in any ratio.

The present invention includes all possible isomers including racemates and optically pure forms of compound of formula I. Said forms can be prepared by using conventional techniques known in the art such as by use of chiral reagents or other methods.

As disclosed herein the term "salts" mean acid addition of base addition salts of the compound of invention. In particular the salts include "the pharmaceutically acceptable salts" which refer to salts that retain the biological effectiveness and effectiveness of the compound of invention while not having any biologically or otherwise unwanted properties such as toxicity or causing any kind of formulation difficulties.

Pharmaceutically acceptable acid addition salts can be formed with organic acids and/or inorganic acids. Acid addition salts of the compound according to present invention can be selected from a group comprising; acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Pharmaceutically acceptable base addition salts can be formed with organic bases and/or inorganic bases. Bases appropriate for preparation of base addition salts of the compound of the invention can be selected from sodium hydroxide, sodium carbonate, sodium bicarbonate, calcium hydroxide, calcium carbonate, calcium bicarbonate, magnesium hydroxide, magnesium carbonate, magnesium bicarbonate, potassium hydroxide, potassium carbonate, potassium bicarbonate and the like.

As disclosed herein the term "isotopically labeled compounds" refers to compounds of formula I wherein one or more atoms are replaced with an atom having selected atomic mass or mass number. Such replacements can be made with for example; $^{2}H$, $^{3}H$, $^{11}C$, $^{13}C$, $^{14}C$, $^{15}N$, $^{18}F$ $^{31}P$, $^{32}P$, $^{35}S$, $^{36}Cl$, $^{125}I$. Such isotopically labaled variants of compound of the invention can be used for detection or imaging techniques known in the art or for radioactive treatment of patients.

p53 refers to the human protein itself as described by Matlashewski et al. in EMBO J. 3, 3257-62 (1984) or related family members. MDM2 (especially when mentioned as MDM2 or variants thereof) generally refers to all genes and/or proteins encoded thereof with the names MDM2, Mdm2, HDM2, Hdm2, or a variant thereof.

In another aspect present invention relates to pharmaceutical compositions comprising compound of formula I, DRG-MDM2-3, or a pharmaceutically acceptable derivative thereof and at least one pharmaceutically acceptable excipient.

In a preferred embodiment of the invention, the pharmaceutically acceptable excipient can be selected from a group comprising; solvents, antioxidants, preservatives (e.g. antibacterial agents, antifungal agents), isotonic agents, absorption delaying agents, sats, preservatives, stabilizers, binders, disintegrants, lubricants, sweetening agents, flavoring agents and combinations thereof. Particular examples of each group are disclosed in Remington's Pharmaceutical Sciences, 18th Ed. Mack Printing Company, 1990 and incorporated herein by reference.

The pharmaceutical compositions comprising compound of formula I can be formulated for different routes of administration. In an embodiment of the invention, pharmaceutical compositions comprising compound of formula I can be formulated for oral administration, parenteral administration, topical administration or rectal administration.

In a preferred embodiment of the invention, pharmaceutical compositions of the invention for oral administration can be in the form of tablets, lozenges, aqueous or oily suspensions, dispersible powders or granules, emulsion, hard or soft capsules, or syrups or elixirs.

In a preferred embodiment of the invention, pharmaceutical compositions of the invention for parenteral administration can be in the form of isotonic solutions or suspensions or in to form of lyophilized powder suitable for reconstitution prior to administration. Said pharmaceutical compositions of the invention for parenteral administration can be for intramuscular, intravenous, subcutaneous, intraperitoneal, intratracheal administration.

In a preferred embodiment of the invention, pharmaceutical compositions of the invention for topical administration can be in the form of aqueous solutions, suspensions, ointments, pastes, lotions, transdermal patches, gels, creams, or sprayable formulations such as aerosols. Such topical administration covers administration through skin, eye or nose (i.e. intranasal administration). Thus, pharmaceutical compositions of the invention can be in the form of dry powders, solutions or aerosols for administration through pressurized containers, pump, spray, atomizer or nebulizer with or without a suitable propellant.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

In another aspect the invention relates to compound of formula I, DRG-MDM2-3, or a pharmaceutically acceptable derivative thereof for use in treatment of a disorder where p53-MDM2 interaction plays a role.

In a preferred embodiment, the invention, relates to compound of formula I, DRG-MDM2-3, or a pharmaceutically acceptable derivative thereof for use in treatment of a disorder mediated by the activity (including normal activity or especially over activity) of MDM2.

In a preferred embodiment, a disorder mediated by the activity of MDM2 is a proliferative disease such as cancer.

In an embodiment of the invention, cancer includes benign or malignant tumors, a soft tissue sarcoma or a sarcoma (e.g. liposarcoma, rhabdomyosarcoma) or bone cancer (e.g. osteosarcomas), a carcinoma (e.g. such as of the brain, kidney, liver, adrenal gland, bladder, breast, gastric, ovary, colon, rectum, prostate, pancreas, lung, vagina or thyroid), a glioblastoma, meningioma, glioma, mesothelioma, a multiple myeloma, a gastrointestinal cancer (especially colon carcinoma or colorectal adenoma), a tumor of the head and neck, a melanoma, a prostate hyperplasia, a neoplasia, a neoplasia of epithelial character, a leukemia such as acute myeloid leukemia or B-cell chronic lymphocytic leukemia, a lymphoma (such as of B- or T-cell origin) and metastases in other organs.

In another aspect the invention relates to the use of a compound of formula I or salt thereof as defined herein, for the manufacture of a medicament for the treatment of a disorder or a disease in a subject mediated by the activity of MDM2.

In another aspect, the invention relates to the use of a compound of formula I or a salt thereof as defined herein to induce cell cycle deceleration or preferably arrest and/or apoptosis in cells containing p53 or variants thereof that are still functional, for sensitizing cells to one or more additional pharmaceutically active agents, such as inducers of apoptosis and/or of cell cycle deceleration or arrest.

In another aspect, the invention relates to combinations comprising compound of formula I and one or more additional active agent selected from a group comprising; anti-proliferative agents, immunomodulatory agents, antiviral agents, antimicrobial agents, anti-infective agents, anti-inflammatory agents, anesthetic agents, antiemetics or combinations thereof where appropriate. In a preferred embodiment additional active agent is one or more anti-proliferative agent.

In an embodiment of the invention, anti-proliferative active agent can be one or more of the agents selected from the group comprising but not limited to; alkylating agents, anthracyclines, taxanes (cytoskeletal disruptors), epothilones, histone deacetylase inhibitors, inhibitors of topoisomerase I, inhibitors of topoisomerase II, kinase inhibitors, tyrosine kinase inhibitors, nucleotide analogs and precursor analogs, peptide antibiotics, platinum based agents, retinoids, vincaalkaloids and derivatives or other agents.

Alkylating agents can be selected from a group comprising but not limited to; bendamustine, cyclophosphamide, mechlorethamine, chlorambucil, melphalan, dacarbazine, nitrosoureas, streptozotocin, temozolomide, trabectedin.

Anthracyclines can be selected from a group comprising but not limited to; daunorubicin, doxorubicin, epirubicin, idarubicin, mitoxantrone, valrubicin.

Taxanes (cytoskeletal disruptors) can be selected from a group comprising but not limited to; paclitaxel, docetaxel, abraxane, taxotere, cabazitaxel, Epothilones can be selected from a group comprising but not limited to; epothilone A, epothilone B, epothilone C, epothilone D, epothilone E, epothilone F or pharmaceutically acceptable derivatives thereof such as ixabepilone.

Histone deacetylase inhibitors can be selected from a group comprising but not limited to; belinostat, panobinostat, valproate, vorinostat, romidepsin.

Inhibitors of topoisomerase I can be selected from a group comprising but not limited to; irinotecan, topotecan.

Inhibitors of topoisomerase II can be selected from a group comprising but not limited to; etoposide, teniposide, tafluposide.

Kinase inhibitors can be selected from a group comprising but not limited to; bortezomib, erlotinib, gefitinib, imatinib, vemurafenib, vismodegib.

Tyrosine kinase inhibitors can be selected from a group comprising, but not limited to, afatinib, axitinib, bosutinib, cobimetinib, crizotinib, dasatinib, erlotinib, gefitinib, imatinib, lapatinib, nilotinib, osimertinib, pazopanib, ruxolitinib, sunitinib, vandetanib.

Nucleotide analogs and precursor analogs can be selected from a group comprising but not limited to; azacitidine, azathioprine, cladribine, clofarabine, capecitabine, cytarabine, doxifluridine, decitabine, floxuridine, fludarabine, fluorouracil (5-FU), fluorouracil, gemcitabine, hydroxyurea, mercaptupurine, methotrexate, nelarabine, pentostatin, tioguanine, trifluridine, tipiracil.

Peptide antibiotics can be selected from a group comprising but not limited to; bleomycin, actinomycin.

Platinum based agents can be selected from a group comprising but not limited to; carboplatin, cisplatin, oxaliplatin.

Retinoids can be selected from a group comprising but not limited to; tretinoin, alitretionoin, bexarotene, isotretinoin, tamibarotene.

Vincaalkaloids and derivatives can be selected from a group comprising but not limited to; vinblastine, vincristine, vindestine, vinflunine, vinorelbine.

Other agents can be selected from a group comprising but not limited to; methotrexate, pemetrexed, pralatrexed, raltitrexed, etoposide teniposide, abiraterone, bicalutamide, cyproterone, degarelix, exemestane, fulvestrant, goserelin, histrelin, leuprolide, mifepristone, triptorelin, lenalidomide, pomalidomide, thalidomide, everolimus, temsirolimus, anagrelide, ceritinib, dabrafenib, idelalisib, ibrutinib, palbociclib, vemurafenib, bleomycin, dactinomycin, eribulin, estramustine, ixabepilone, mitomycin, procarbazine, alectinib, fluxymesterone, iobenguane, imiguimod, interferon, ixazomib, lanreotide, lentinan, octreotide, omacetaxine, tegafur, gimerazil, oteracil, uracil, combretastatin.

In an embodiment of the invention, such combinations can be in a form wherein compound of formula I and one or more therapeutically active agents, preferably anti-proliferative agents are formulated together.

In another embodiment of the invention, compound of formula I and one or more therapeutically active agents, preferably anti-proliferative agents are formulated separately but they are administered to a patient in need thereof simultaneously or sequentially.

Comprising in the context of the present specification is intended to meaning including.

Where technically appropriate, embodiments of the invention may be combined.

Embodiments are described herein as comprising certain features/elements. The disclosure also extends to separate embodiments consisting or consisting essentially of said features/elements.

Technical references such as patents and applications are incorporated herein by reference.

Any embodiments specifically and explicitly recited herein may form the basis of a disclaimer either alone or in combination with one or more further embodiments.

The invention will now be described with reference to the following examples, which are merely illustrative and should not in any way be construed as limiting the scope of the present invention.

EXAMPLES

Example 1: Cell Culture Experiments

HCT 116 colon cancer and MDA-MB231 breast cancer cell lines are used in cell culture experiments.

Cells were treated with high-glucose DMEM medium (Biosera) supplemented with 10% FBS (Gibco) and 1× penicillin/streptomycin (Multicell). The assay was designed to contain 10,000 cells for each well of 24-well cell culture plates before being treated with inhibitors.

Compound of formula I was dissolved with DMSO as 20 mM stock. 24 hours later, the solution was diluted in DMEM with 10% FBS and final concentration of vehicle DMSO was 0.5% at maximum. Therefore, the vehicle group included 0.5% DMSO concentration in experiments. Intensive cultivation of cells causes a decrease in proliferation capacity. Therefore, the confluency did not exceed 60%.

The MTT cell viability assay was used to detect values of half-maximal inhibitory concentration ($IC_{50}$). Different concentrations of compound of formula I ranging between $10^{-9}$ to $10^{-4}$ M were tested on MDA-MB231 cell lines with single dose of treatment. 570 nm absorbance values were recorded and $IC_{50}$ values were calculated by dose response—inhibition curves and nonlinear regression analysis on Graphpad Prism 8 software. $IC_{50}$ value of compound of formula I was determined to be 41 μM (FIG. 1).

EXAMPLE 2: CELL PROLIFERATION INHIBITION ANALYSIS

For proliferation inhibition analysis, cells were seeded in 24 well plates at $1\times10^4$ cells/well cells overnight without drug treatment. During the cell proliferation experiments, we performed five days of treatment in each cell line and repeated the experiments three times to check each experiment. No significant difference in cell viability was observed after the third day. Therefore, cells with different drug concentrations were treated for two days. After 48 hours, MTT was applied to the cells and incubated at 37° C. for 4 hours, formazan was solubilized with DMSO (Sigma-Aldrich, St. Louis, USA) and absorbance was measured at 570 nm.

Figure 2:
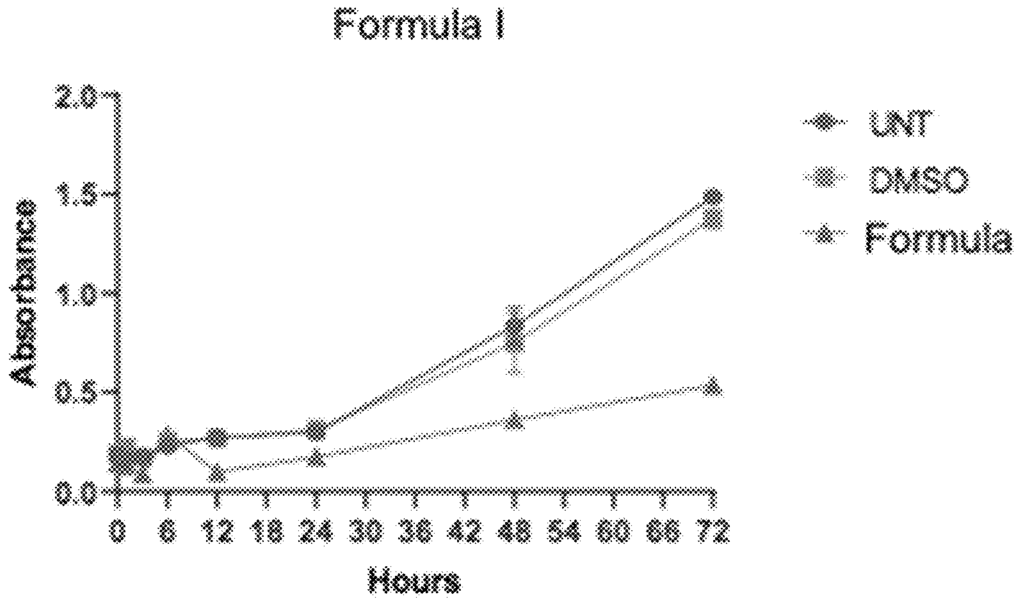

MTT cell proliferation assay results are shown in FIG. 2. Molecule concentration was 100 μM, the lower concentrations were not shown. Vehicle represents the groups treated with only %0,5 DMSO and Untreated represents no molecule treated group. Molecule responses were evaluated by cell viability which is obtained by spectrophotometric analysis of cells upon MTT treatment at 12 h, 24 h, 48 h and 72 h. Molecule groups showed statistically significant difference compared to vehicle and untreated groups. Statistical significance in graphs was determined by comparing each treatment group with DMSO control using ANOVA testing and significance is considered as $p<0.001$ (FIG. 2).

Figure 3:
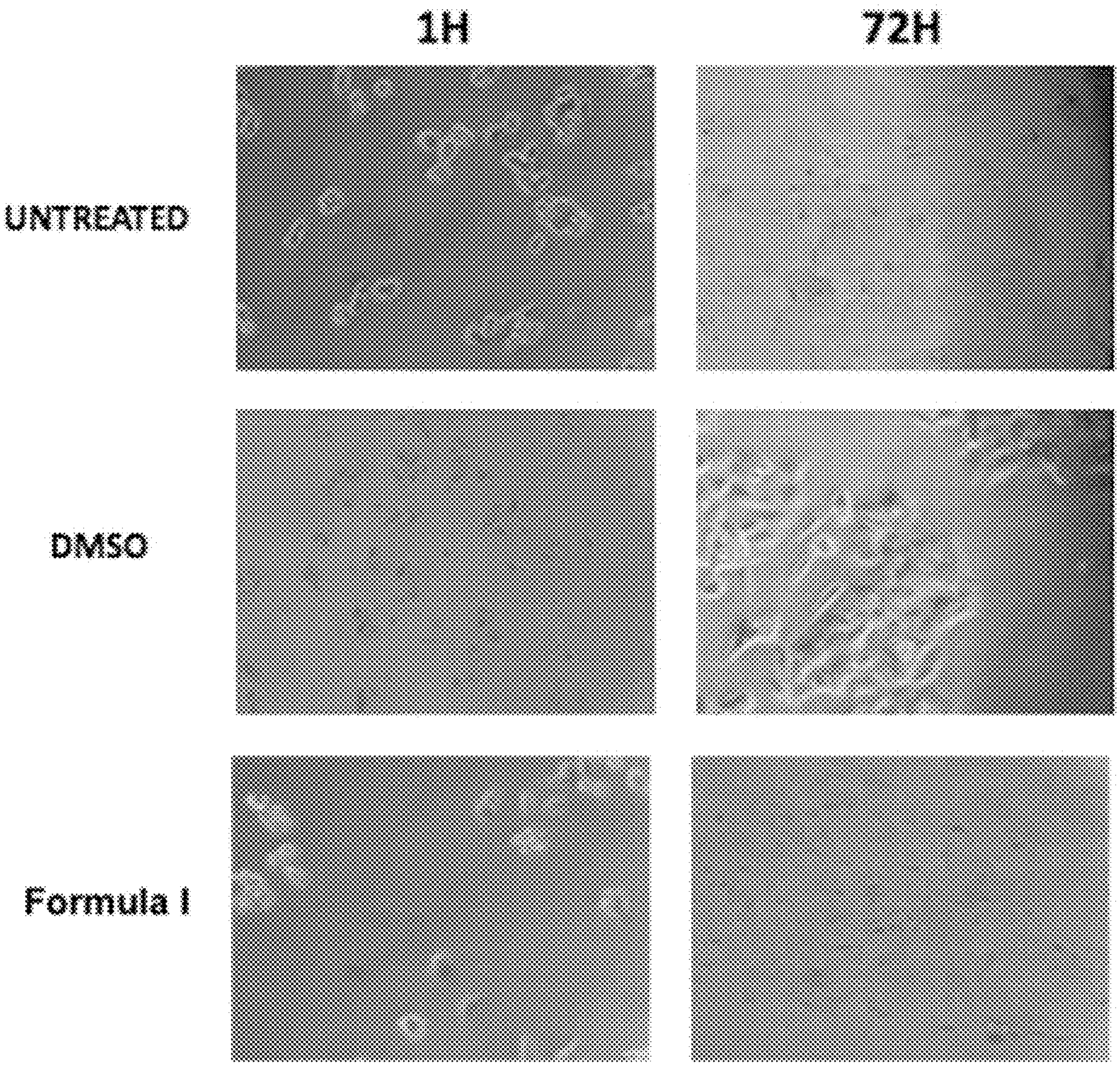

Microscopic evaluation of HCT-116 cells are shown in FIG. 3. Cells were photographed and observed under microscope for three days. Vehicle group showed neat proliferation of cells as untreated group did, whereas molecule treated group showed reduced proliferation and showed apoptotic cell structures. Compound of formula I showed clear apoptotic activity from the twelfth hour (FIG. 3).

As a result, cell viability decreased by 40% at the end of the first day and reached 60% at the end of the third day. Any cell proliferation change and apoptotic cell morphology were not observed in the untreated and vehicle groups. Moreover, differences in cell morphology were also observed. Unlike normal cells, the formation of circular cell structure was observed in apoptotic cells (FIG. 3). Upon treatment with the compound of formula I according to present invention with 100 μM concentration, cells having the morphology of apoptotic cells were observed starting from the 3$^{rd}$ hour.

The invention claimed is:

1. A method of treating a disorder in a subject in need thereof, wherein p53-MDM2 interaction plays a role in the disorder, the method comprising the step of administering to the subject a composition comprising a therapeutically effective amount of a compound of Formula I, or a pharmaceutically acceptable derivative thereof Formula I (DRG-MDM2-3)

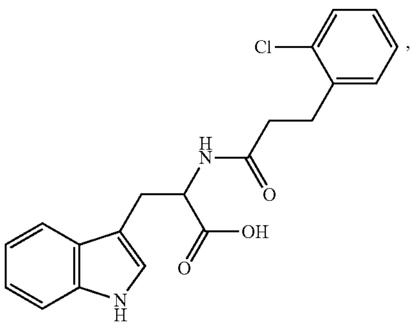

wherein the pharmaceutically acceptable derivative of Formula I comprises Formula Ia, Formula Ia

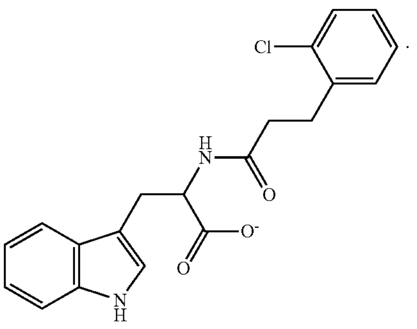

2. The method of claim 1, wherein the disorder is a proliferative disease.

3. The method of claim 2, wherein proliferative disease is a cancer.

4. The method of claim 3, wherein the cancer is a benign or malignant tumor, a soft tissue sarcoma or a sarcoma or bone cancer, a carcinoma, a glioblastoma, meningioma, glioma, mesothelioma, a multiple myeloma, a gastrointestinal cancer, a tumor of the head and neck, a melanoma, a prostate hyperplasia, a neoplasia, a neoplasia of epithelial character, a leukemia or a lymphoma.

5. The method of claim 1, wherein the compound of formula I, or a pharmaceutically acceptable derivative thereof, is administered in combination with one or more additional pharmaceutically active agents.

6. The method of claim 5, wherein the one or more additional pharmaceutically active agents are selected from the group consisting of anti-proliferative agents, immunomodulatory agents, antiviral agents, antimicrobial agents, anti-infective agents, anesthetic agents, antiemetics, and combinations thereof.

7. The method of claim 6, wherein the anti-proliferative agents are selected from the group consisting of alkylating agents, anthracyclines, taxanes or cytoskeletal disruptors, epothilones, histone deacetylase inhibitors, inhibitors of topoisomerase I, inhibitors of topoisomerase II, kinase inhibitors, tyrosine kinase inhibitors, nucleotide analogs and nucleotide precursor analogs, peptide antibiotics, platinum-based agents, retinoids, *vinca* alkaloids, methotrexate, pemetrexed, pralatrexate, raltitrexed, etoposide, teniposide, abiraterone, bicalutamide, cyproterone, degarelix, exemestane, fulvestrant, goserelin, histrelin, leuprolide, mifepristone, triptorelin, lenalidomide, pomalidomide, thalidomide, everolimus, temsirolimus, anagrelide, ceritinib, dabrafenib, idelalisib, ibrutinib, palbociclib, vemurafenib, bleomycin, dactinomycin, eribulin, estramustine, ixabepilone, mitomycin, procarbazine, alectinib, fluoxymesterone, iobenguane, imiquimod, interferon, ixazomib, lanreotide, lentinan, octreotide, omacetaxine, tegafur, gimeracil, oteracil, uracil, and combretastatin.

8. The method of claim 1, wherein the composition further comprises a pharmaceutically acceptable excipient.

9. The method of claim 8, wherein the disorder is a cancer.

10. The method of claim 9, wherein the cancer is a benign or malignant tumor, a soft tissue sarcoma or a sarcoma or bone cancer, a carcinoma, a glioblastoma, meningioma, glioma, mesothelioma, a multiple myeloma, a gastrointestinal cancer, a tumor of the head and neck, a melanoma, a prostate hyperplasia, a neoplasia, a neoplasia of epithelial character, a leukemia or a lymphoma.

11. The method of claim 1, wherein the composition further comprises one or more additional pharmaceutically active agents selected from the group consisting of anti-proliferative agents, immunomodulatory agents, antiviral agents, antimicrobial agents, anti-infective agents, anesthetic agents, antiemetics, and combinations thereof.

12. The method of claim 11, wherein the disorder is a cancer.

13. The method of claim 12, wherein the cancer is a benign or malignant tumor, a soft tissue sarcoma or a sarcoma or bone cancer, a carcinoma, a glioblastoma, meningioma, glioma, mesothelioma, a multiple myeloma, a gastrointestinal cancer, a tumor of the head and neck, a melanoma, a prostate hyperplasia, a neoplasia, a neoplasia of epithelial character, a leukemia or a lymphoma.

14. The method of claim 4, wherein:

the sarcoma is liposarcoma or rhabdomyosarcoma;

the carcinoma is of the brain, kidney, liver, adrenal gland, bladder, breast, gastric, ovary, colon, rectum, prostate, pancreas, lung, vagina, or thyroid;

the gastrointestinal cancer is colon carcinoma or colorectal adenoma;

the leukemia is acute myeloid leukemia or B-cell chronic lymphocytic leukemia; and the lymphoma is of B- or T-cell origin.

* * * * *